(12) United States Patent
Hatfield et al.

(10) Patent No.: US 6,721,055 B2
(45) Date of Patent: Apr. 13, 2004

(54) PARTICLE DISPERSION DETERMINATOR

(75) Inventors: James Henry Hatfield, Husthwaite (GB); Peter Barry Howard, Yarm (GB); Edmund John Lawson, Stockton-on-Tees (GB); Alastair Orr Mackenzie, Darlington (GB)

(73) Assignee: Tioxide Group Services Limited, London (GB)

( * ) Notice: Subject to any disclaimer, the term of this patent is extended or adjusted under 35 U.S.C. 154(b) by 150 days.

(21) Appl. No.: 10/020,789

(22) Filed: Dec. 14, 2001

(65) Prior Publication Data

US 2002/0067485 A1 Jun. 6, 2002

Related U.S. Application Data

(63) Continuation-in-part of application No. 09/308,348, filed as application No. PCT/GB98/02494 on Aug. 20, 1998.

(30) Foreign Application Priority Data

Aug. 21, 1997 (GB) ............................................. 9717658

(51) Int. Cl.$^7$ .......................... G01N 21/55; G01N 15/02
(52) U.S. Cl. ....................................... 356/445; 356/336
(58) Field of Search ................................ 356/445, 335, 356/336, 338, 237.1, 237.3

(56) References Cited

U.S. PATENT DOCUMENTS 5,249,029 A * 9/1993 Sommer et al. ............ 356/336

* cited by examiner

Primary Examiner—Frank G. Font
Assistant Examiner—Roy M. Punnoose
(74) Attorney, Agent, or Firm—Russ R. Stolle; Ron D. Brown; Christopher J. Whewell

(57) ABSTRACT

Provided herein is a device useful for measuring the fineness of a dispersion of particles in a liquid vehicle. A device according to the invention includes a light source, a means for mounting a film of said vehicle of increasing thickness, and a means for producing an electronic image of said film, in which these elements are positioned relative to one another so that the light the imaging means receives is predominantly light reflected from regions of the surface of said film which are disrupted by protruding particles. This is achieved by configuring the device so that the image producing means is aimed into the dark field below the light source, with the image producing means being directed generally at an angle below the angle of reflection of any light reflected from undisrupted regions of the surface of the film. In one preferred embodiment, the image producing means is oriented to be inclined at an angle of approximately 12 degrees to the plane of the surface of the moveable carrier which is part of the means for mounting a film.

23 Claims, 3 Drawing Sheets

PARTICLE DISPERSION DETERMINATOR

CROSS-REFERENCE TO RELATED APPLICATIONS

This application is a Continuation-In-Part of and claims priority to, U.S. patent application Ser. No. 09/308,348 filed May 19, 1999, which is currently pending.

TECHNICAL FIELD

This invention relates to a device useful for determining the degree of dispersion of particles in a particle/vehicle system, such as liquid coatings and their intermediates. The invention relates more particularly to a machine combination that is especially well-suited for determining the degree of dispersion of particulate materials, including pigments, extenders, and fillers used in paints and coatings, and methods for using the combination.

BACKGROUND

Various properties of a coating are influenced to a large extent by the size of the particulate materials present at the coating surface, including the opacity, color, shade, tint, gloss, and weatherability. In order to achieve optimized physical and performance properties from a coating, it is generally found that there exists an optimum range of sizes for the particles for the particular intended use or application under consideration. Thus, for particulate materials which are intended for use in paints, it is necessary to cause the particles to possess a maximum particle size. This is most frequently achieved by using a mill or otherwise grinding the pigment to a relatively uniform grind size prior to its dispersion into a vehicle, such as a paint formulation, to achieve the desired maximum size and in particular to break up particle agglomerations. Since it is generally undesirable from the standpoint of capital resources to employ excessive milling when grinding the particles, it has been found beneficial by those in the industry to employ precise and accurate test methods for determining the size distribution to which the particles have been ground or milled. Such tests are generally referred to as "fineness of grind" tests, and these typically give a measure of the maximum size present in the sample tested.

By far the most popular test method which is used in the art is set forth in the specification of ASTM D-1210. The main hardware component used in this Standard test is a solid rectangular gauged block having a flat top surface and which incorporates either a single shallow channel or two parallel shallow channels machined into this surface. Each channel is tapered uniformly in depth along its length dimension from a depth of zero at one end, to a specified depth, e.g. 50 or 100 $\mu$m, at the other end. There are calibration marks disposed along the length of the channel(s) at graduated depths so as to form a scale, wherein each mark corresponds to the depth at that point. Often, such gauges are calibrated in terms of Hegmann units, a scale that is well-known to those skilled in the art of particle size determination. In use, a sample to be tested is placed at the deep end of a channel of increasing depth as per the above so that it overflows the walls of the channel slightly, and is subsequently drawn down the path towards the shallow end using a flat scraper blade of suitable dimension. The gauged block containing sample in the channel is then disposed between the operator and a light source, and observation is made of the point along the scale at which a definite speckled pattern (as distinct from isolated specks) first appears. Location of this point gives a measure of the degree of the fineness of the grind. In addition the point at which "stragglers", i.e., isolated particles as distinct from a definite speckled pattern, first appear can be assessed. The sample can then be assigned a grading based on the observation of where these points lie on the scale.

However, this type of testing has its drawbacks. First, such test methods are subjective, as the assessment result obtained depends on the personal observation and judgement by a human operator as to where along the scale the above-mentioned features lie. Since the point on the scale at which these features occur is not sharply defined, there exists some latitude for personal interpretations and biases of the observer to influence the final results obtained, and it is quite common for different operators to record different results for the same sample of material. Secondly, it is important that the assessment by the observer be carried out before the sample dries to any appreciable extent, which is within 10 seconds according to the Standard. The reason that a quick observation is necessary is that the thickness of sample films generally decrease during drying. The 10-second limit often makes assessment by the operator a difficult task. Thirdly, once the test has been completed and the gauge cleaned prior to a subsequent determination, no physical record remains other than the assessment figures recorded by the operator.

Thus, if a reasonably-priced method or device were available by which operator bias could be substantially reduced or eliminated and which would produce a permanent record of a particle size determination for any specific sample of particulate material, such method or device should be welcomed by the industry.

U.S. Pat. No. 5,249,029, which is fully incorporated herein by reference thereto, discloses an apparatus that meets these requirements, which apparatus embodies the features of: a) a light source with a focussing lens for producing a light spot on the paint surface to be investigated; b) a dark-field lens comprising an objective for collecting the scattered light emanating from particles illuminated by the light spot and an aperture diaphragm for eliminating the light directly reflected at the paint surface; c) a photoreceiver connected to an evaluation circuit for detecting, recording and further processing the scattered light signals; and d) a scanner for longitudinally scanning the sample channel. The scanner consists of a synchronous motor by which the grindometer block is longitudinally displaced on a carriage linearly as a function of time, the light spot moving over the paint surface to be investigated. According to a preferred embodiment, the scattered light signals are counted by the evaluation circuit in zones along the paint surface during scanning. To this end, a narrow slot laterally disposed to the sample channel is provided in front of the detector and improves zone resolution. This invention of the prior art alleges the following advantages: 1) application and stripping of the paint surface on the grindometer block is followed by fully automatic, objective measurement; 2) measurement of the particle size distribution accords very well with the conventional visual evaluation; 3) the reproducibility of the apparatus is sufficient for all purposes; and 4) measurement of the particle size distribution is possible for all the usual colors.

However, the invention disclosed in U.S. Pat. No. 5,249,029 is not without inherent disadvantages. For example, the apparatus described therein is confined to the use of a laser source to provide the required virtual point source. Further, the apparatus described therein requires a focusing lens to direct the laser beam onto the paint surface. This apparatus also requires receiving optics that provide for the exclusion of ambient light by means of a narrow-band, 633 nm filter, dark-field optics incorporating a central beam block to exclude specular reflected laser light, and a slot to improve data resolution in the scan direction. This apparatus further employs a single silicon photodetector responding to the average level of scattered light across the full width of the paint channel in the grindometer block. Thus, it cannot distinguish individual particles protruding through the surface of the paint film where two or more particles are arranged on a transverse line. Finally, the apparatus of U.S. Pat. No. 5,249,029 does not read the standard scale marks on the grindometer gauge.

SUMMARY OF THE INVENTION

The present invention comprises a combination useful for assessing the fineness of dispersion of particles in a liquid vehicle, and comprises: a light source; a moveable carrier having a top surface; a grindometer gauge block disposed on the top surface of the carrier. The block has a longest length dimension and a flat face surface, and comprises a linear channel disposed on its face that varies in depth along the length dimension and has corresponding markings to indicate the depth of the channel. The channel is adapted to receive a liquid vehicle which contains a film-forming dispersion of particles. There is an image-producing means, useful for producing a two-dimensional electronic image of a film disposed in said channel from a liquid vehicle placed therein, and a memory means for archiving said two-dimensional electronic image of the film. There is also a means for displaying said two-dimensional image of said film. The light source, grindometer gauge block, and image-producing means are sufficiently positioned so that the view of the image-producing means is aimed into the dark field below the light source so as to render the image-producing means to be disposed so that the light it receives is predominantly that which is reflected from discontinuities in the surface of said film. In this context, "predominantly" means at least 95% of the light on the basis of total energy, for the purposes of this specification and the appended claims.

DETAILED DESCRIPTION

According to the present invention, there is provided a combination for assessing the fineness of dispersion of particles in a liquid vehicle, which combination comprises: a light source, means for mounting a film of said vehicle of increasing thickness, and an image producing means for producing an electronic image of the film. The light source, mounting means, and image-producing means are preferably positioned relative to one another so that said image producing means receives predominantly light reflected from regions of the surface of said film which are disrupted by protruding particles.

According to another aspect of the invention, a device for assessing the fineness of dispersion of particles in a liquid vehicle comprises a light source, a line scan video camera mounted at an acute angle to the horizontal so that the angle of view is below the angle of illumination, a moveable carrier lying between the light source and the camera and movable relative to the camera, wherein the carrier comprises a means for accurately positioning a fineness of grind gauge block, and means for storing and/or displaying images generated by the camera.

According to a further aspect of the invention, there is provided a method for assessing the fineness of dispersion of particles in a liquid vehicle comprising drawing down a sample of the vehicle to form a film of increasing thickness, illuminating said film with a light source and generating an electronic image of said film.

Figure 1:
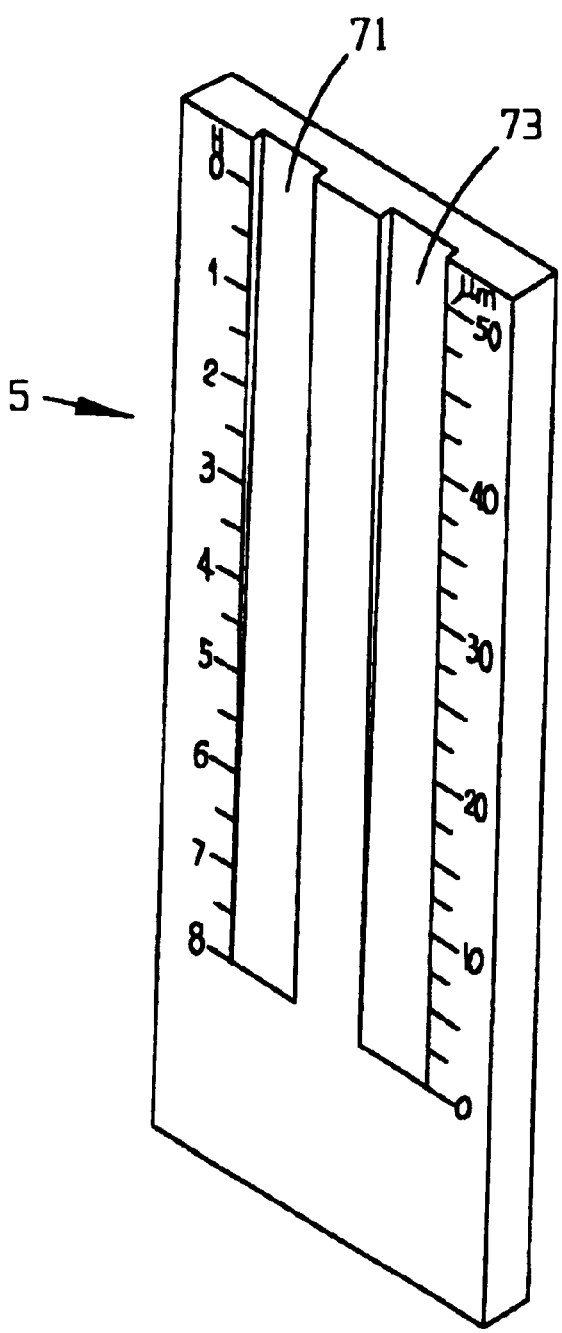
FIG. 1 shows a gauge block of the type specified in the ASTM Standard.

Referring to the drawings and initially to FIG. 1 there is shown a gauged grindometer block 5 according to the prior art that is useful for determining particle grind sizes. One such block suitable for use in the present invention is available from Sheen Instruments Ltd. of Kingston, England under the designation "501/50". In this rectangular solid block, there are two channels 71 and 73 machined into the surface of the block, each having a depth which tapers along its length from a depth of zero to a depth of about 50 microns. Other blocks having similar features are useful as an element of the present invention, provided they have a channel of suitably varying depth disposed on their top surface.

Figure 2:
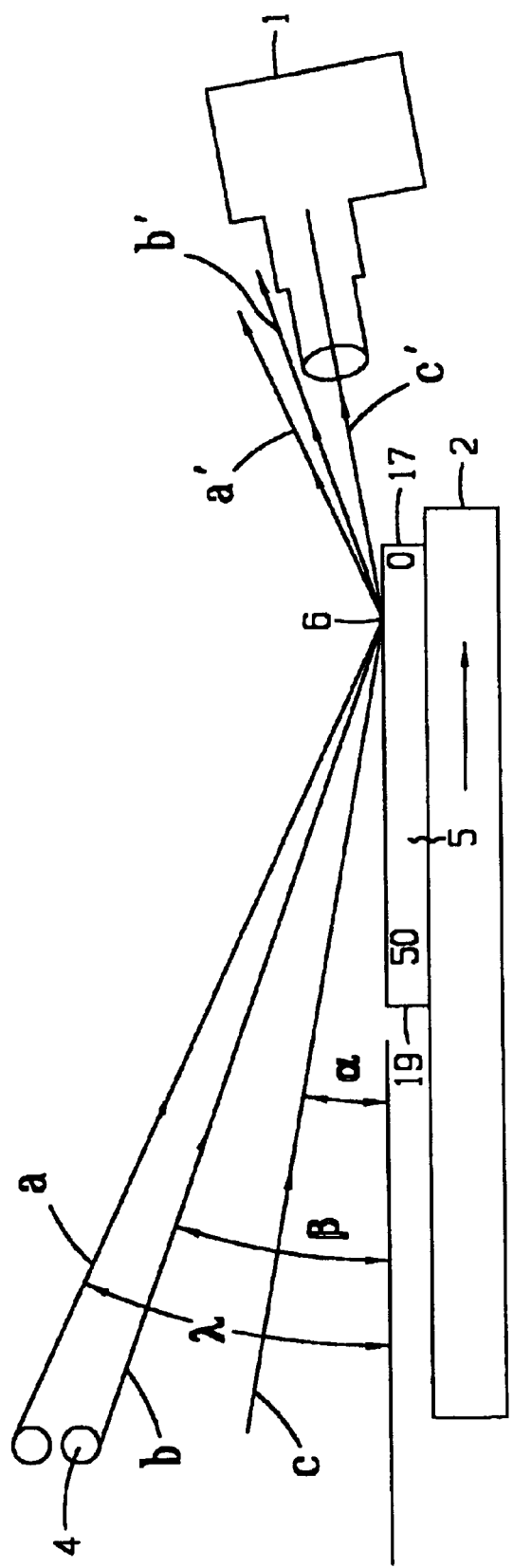
FIG. 2 is a diagrammatic view of one embodiment of the device according to the invention.

FIG. 2, shows a combination according to the invention which comprises a flat moveable carrier 2 having a top surface with a gauged grindometer block 5 affixed thereon. In addition to the machined channels 71 and 73, the gauged block has a first end portion 17, and a second end portion 19. Disposed above the plane of the surface of the moveable carrier 2 beyond the first end portion 17 of the gauged grindometer block 5 is an image recording means 1. According to one preferred form of the invention, the image recording means 1 is oriented so that its lens is disposed at an inclination which provides an angle of approximately 12° with respect to the surface of the moveable carrier 2.

There is a light source 4 disposed above the plane of the surface of the moveable carrier 2 beyond the second end portion 19 of the gauged grindometer block 5. The light source 4 is mounted at an effective height to enable the camera to view the "dark field" below the light source through reflection in the free surface of the film formed from the liquid vehicle.

In use, a sample to be tested is drawn down into either of the channels 71 or 73 of the block as shown in FIG. 1, and the block is immediately secured to the moveable carrier 2 and oriented with the deep end of the channel away from the camera so that the deepest portion of the channel in gauged grindometer block 5 corresponds with the second end portion 19 as shown in FIG. 2. Activation of the drive motor causes the gauge block to move at a constant speed in the direction indicated by the arrow in FIG. 2 and past a point 6 on which the camera is focussed, in one preferred form of the invention over a period of about 3 seconds, so that an image is built up line-by-line. Under such conditions, particles projecting through or distorting the surface of the sample film direct light into the camera. Scanning in this manner avoids depth-of-focus problems and allows a wide lens aperture to be used, so maximizing the amount of light collected. It is preferable to scan the shallow end of the channel first in order to reduce bias due to the drying of the sample, which is more significant at the shallow end of the channel.

The example which follows is illustrative of the invention, but should not be considered delimitive thereof in any way.

EXAMPLE

Figure 3:
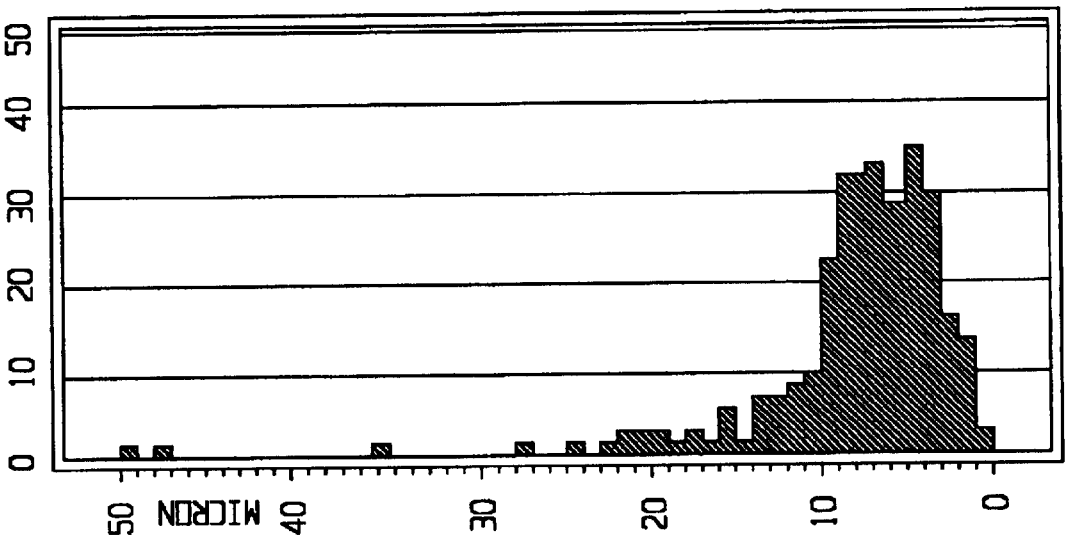
FIG. 3 shows the speckle pattern produced during a test of a paint by the device of FIG. 2 and an analysis of the pattern in the form of a bar chart.
Figure 3:
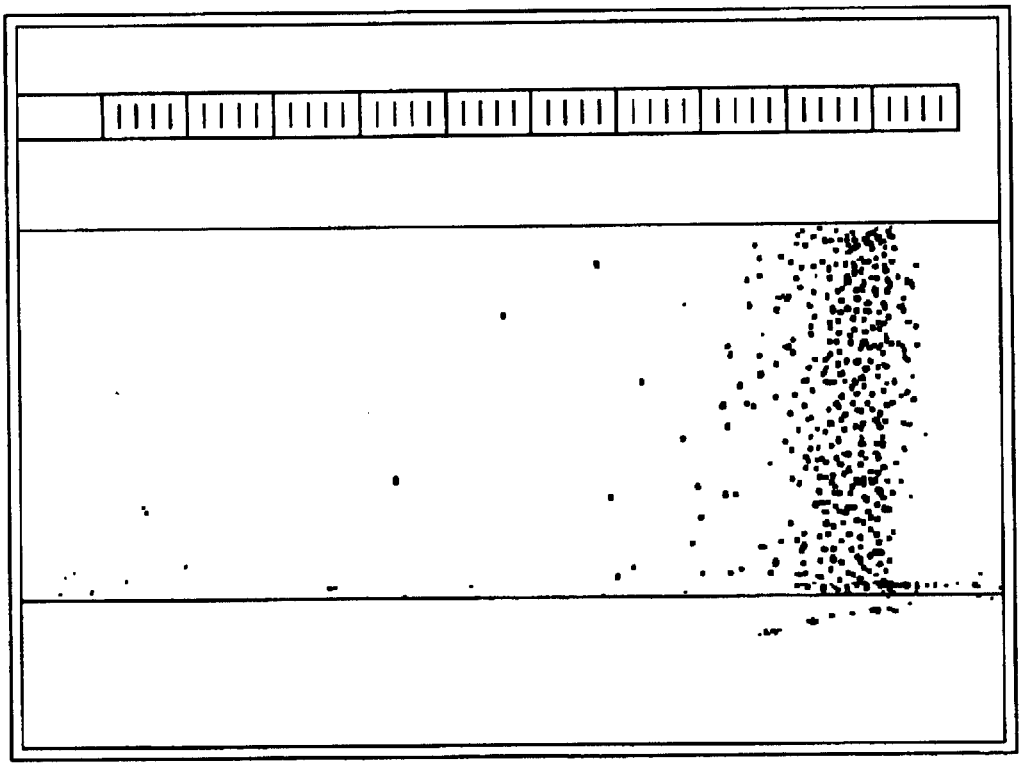

A paint sample consisting of titanium dioxide pigment in an alkyd resin vehicle was dripped on to a 50 µm gauge block and drawn down to form a film of decreasing thickness as specified in ASTM D-1210. The block was immediately placed in the device shown in FIG. 2 and the film was scanned as previously described. The image produced is shown (black-white reversed for clarity here only) in FIG. 3 and computer analysis gave a fineness of grind reading of 10–21. Assessment of the sample by three different men using the conventional method gave readings of 10–20, 9–20, and 11–22 respectively. Further computer analysis produced the bar chart shown in FIG. 3 and as can be seen, this gives an indication of the number of particles protruding through the film at each point along the length of the gauge channel. For example there are 7 particles protruding where the channel has a depth of 10 to 11 µm.

The Moveable Carrier

The moveable carrier 2 may be caused to move at a specified rate by a synchronous electric motor (not shown) and other wares suitable to make the carrier movable in a longitudinal direction relative to the camera.

In one arrangement, the means for mounting the film comprises a moveable carrier 2, which is movable relative to the image producing means and a means for positioning consistently on the carrier a fineness of grind gauge block incorporating a channel of varying depth.

Whereas the relative movement could be produced by keeping the film fixed and moving the image-producing means, it is preferred that the film is moved. Alternatively, the film and the image-producing means could be fixed and a movable optical path provided, i.e., an arrangement comprising lenses, mirrors, prisms, and optical fibres.

The Light Source

According to a preferred form of the invention, a linear incandescent lamp operating either on a DC supply or at a minimum frequency of 50 Hz or a biaxial compact fluorescent lamp operating at a frequency greater than 5 kHz is employed in order to minimize flicker. A linear quartz halogen lamp is particularly suitable, such as GE QUARTZLINE® K12 Q150 T3/CL of Philips Linear PLUSLINE® 150T3Q/CL/CP.

The Image Producing Means

According to a preferred form of the invention, the image-producing means is a line scan video camera. In order to avoid depth of focus problems, the video camera is focussed on a narrow line and the film is moved relative to the camera at a rate dependent on the line scan rate of the camera so that the image is built up line by line. Alternatively, the image producing device may be any array of photo diodes or charge coupled photodetector elements.

In one preferred form of the invention, the image-producing means is a camera, RETICON® LC1911HKN-011, that provides 1024 contiguous photo-pixels, each 13 µm long and 26 µm wide, and which is preferably fitted with a PENTAX®/COSMICAR® B5018A-3 C-mount lens on 30 mm of extension tube—with the camera supported so that its view is angled between 5 and 20 degrees below the horizontal, and is preferably angled 12 degrees below the horizontal, which horizontal in general coincides with the planar surface of the grindometer block.

The image may be electronically stored so it can be reproduced and, by using a suitably-programmed computer may be analyzed to provide speckle and straggler readings and an output in a different form, such as a histogram bar chart.

Thus, it can be seen that while the apparatus described in U.S. Pat. No. 5,249,029 requires a focusing lens to direct the laser beam onto the paint surface, the present invention employs no input optics of any kind, but only a linear incandescent (tungsten) lamp that serves as an extended optical source. Further, whereas the apparatus described in U.S. Pat. No. 5,249,029 requires specialised receiving optics to provide for exclusion of ambient light by means of a narrow-band, 633 nm filter, dark-field optics incorporating a central beam block to exclude specular reflected laser light, and a slot to improve data resolution in the scan direction; the present invention on the other hand uses a bright linear source to reduce sensitivity to ambient light, employs a standard achromat camera lens in the receiving path and excludes specular reflected light by directing the receiving optics off-axis from the specular reflection. The apparatus described in U.S. Pat. No. 5,249,029 employs a single silicon photodetector responding to the average level of scattered light across the full width of the paint channel in the grindometer block which precludes its distinguishing individual particles protruding through the surface of the paint film where two or more particles are arranged on a transverse line. The present invention on the other hand collects, displays, archives and analyses a two-dimensional image providing for reliable enumeration of every discrete particle.

Finally, while the apparatus of U.S. Pat. No. 5,249,029 does not read the standard scale marks on the grindometer gauge, the present invention does this, requiring no other calibration marks. This feature gives the present invention tolerance to some dimensional variation from one grind gauge to another, and is self-calibrating in this regard.

Software

During use of a system according to the invention, a portion of the paint sample to be assessed is drawn down onto a steel gauge block which is then placed without delay onto the moveable platform of the scanner unit. This employs a line-scan camera in conjunction with a linear quartz halogen lamp set up to provide 'dark field' illumination. Initially the camera is focused on the surface of the paint film a short distance below the 0 μm scale mark. A new image is then acquired under software control. A PC is used to acquire the image progressively by reading image lines from the camera into system memory, meanwhile advancing the gauge block past the camera in such a way as to image the entire right hand paint channel together with its adjacent scale markings. Image formation commences before the 0 μm mark and terminates after the 50 μm mark has been passed. Once the required area has been scanned, the software releases the moveable platform to return to the park position. The software implements a compression algorithm on the acquired image and saves it to disk.

An interface circuit is incorporated into the system's scanner unit to connect the scanner and the line-scan camera to the PC through the parallel port of the PC. At the beginning of a run, the scanner unit operates a relay under program control, switching on the lamp and engaging the platform drive. The interface provides power at +/−12v and +5v to the camera. It also provides a pixel clock signal at 3.2768 MHz and a line clock at 200 Hz (for 50 Hz mains supply).

In the interface unit the differential video signal developed by the camera is buffered by an amplifier and passed to an 8-bit A->D 'flash' converter such as Micro Power Systems "MP 8785". The converter samples the video signal and converts it in real time to an 8-bit digital signal encoding 256 levels of gray. Just one image line is stored every 5 msec in a static RAM buffer, such as Performance Semiconductor P4C116-25PC. This is a 2K×8-bit device, and only 50% of its capacity is used to store the 1024 bytes which comprise a single image line. As the camera is used upside down, the byte at LO address is the image byte from the 'right hand' end of the image line.

The image line is transferred from the camera to the static RAM in the interface in just 312 μsec. This takes place exactly 200 times every second—so the entire image of 710 lines is acquired in 3.55 seconds. Once each line has been transferred to RAM the PC is signaled by a rising edge on the PC (host) interrupt line at parallel port LPT1. The PC has 4.68 msec to read the line image over the parallel port link before it is overwritten by the following line. So the PC must respond promptly to this signal to achieve image integrity (ie. no missing lines). In practice it takes around 2 msec to transfer one line.

When the PC reads a line it transfers it under EPP 1.9 protocol (making use of Auto Data Strobe Registers) to build up an image of 710 lines in system memory [*p], commencing at the corner of the image adjacent to the 0 μm scale mark. The image so transferred has dimensions 710(H)× 1024(W) bytes (8-bit grey scale image). Under WinNT transfer is by default interrupt driven using IRQ7 on LPT1— and all other interrupts except IRQ0 are masked during image acquisition. Under Win95/98, interrupt latency is poor so transfer is achieved instead by polling the host interrupt line.

Once transferred by software defined in the file "TIDAS-.CPP" (a C++ source file) to system memory in the PC, the image is then copied to a second memory space [*q] and at the same time condensed by summing adjacent pairs of pixels in each line to give an image 710(H)×512(W). This removes any 'alternate pixel' clock noise and leaves an image with adequate spatial resolution for later interpretation. Intensity is slightly modulated in the (H) direction by 100 Hz ripple in the lamp output—but this is acceptable. The screen representation of the image is derived from this memory space [*q].

Next the image is compressed to a third memory space [*cmp] using a dictionary-based algorithm, the use of which is well-known in the art, and the purpose of which is simply to save storage space. When re-loaded, the 710(H)×512(W) image [*q] can be reconstructed from this without loss by the corresponding decompression operation.

For screen viewing/printing of the acquired images three 'Windows' BITMAPS are created as required—identified in TIDVIEW1.CPP as [*bm16], [*bmi16] and [*bmg16]. These are 4-bit (16 grey level or 16 color) bitmaps. [*bm16] is derived from [*q] and arranged so that the origin of the image stored on disk appears at the bottom right hand corner of the screen image. It is marked up with a pair of vertical cursor lines and drawn on the LHS of the screen. It is redrawn as required following the patching of image [*q] which arises when image analysis is invoked. [*bmi16] is again derived from image [*q] and is drawn on the RHS of the screen. It displays the image intensity (min, mean, max) for that portion of each line which falls within the cursor lines. [*bmg16] is the histogram defect count plot generated when a 'rating' result is generated. It is displayed in place of [*bmi16]. An 8-bit (256 gray level) bitmap [*bm256] can be formed where a copy of the image is to be written to disk as a device independent bitmap (.DIB)—to be manipulated later by a separate image handling program.

The portion of the image bounded by the two cursor lines and the 0, 50 μm scale marks is thresholded, undergoes connected component labeling and has the defects classified as 'grits' or 'blobs'. Before this can be done the 11 scale marks (5 μm intervals) must be located in the image.

Some information on expected scale location can be read from the image header (IMAGE PARAMETERS). The TIDAS.CPP function FindScale2( ) then attempts to locate the scale. If it fails then FindScale1( ) resumes the task. The found positions are marked up on the screen by patching the image [*q]. If neither routine succeeds then the scale position can be defined manually using the mouse. The position of the scale marks is verified against the expected position by the function CheckPosition( ).

The function FindThreshold( ) establishes the image intensity distribution histogram (pixel count at each intensity level in range 0–>255). The algorithm then finds the first positive-going zero-crossing in the first derivative function of this histogram. A noise margin (default=6) is then added to give the base thresholding level for generation of a binary image.

The function LabelDefects( ) uses a 'connected component labeling' algorithm to generate a binary image and label the discreet objects in it. The image in the 'region of interest' is copied into temporary memory space [*src] and the labeled output appears in a second space [*dest]. The image [*q] is then patched to amend the screen display accordingly. Finally the image is divided into 1 μm slices: 'grits' and 'blobs' are counted in each of 50 slices. These are displayed as a histogram in BITMAP [*bmg16] and drawn to screen.

The function RateSample( ) develops a 'rating' for the sample based on the above histogram. A parameter 'grp1' records the first μm position at which the grit count exceeds a setpoint number. The principal rating parameter 'grp2' for a given image is derived by starting at the 50 μm end of the histogram and applying the following algorithm:

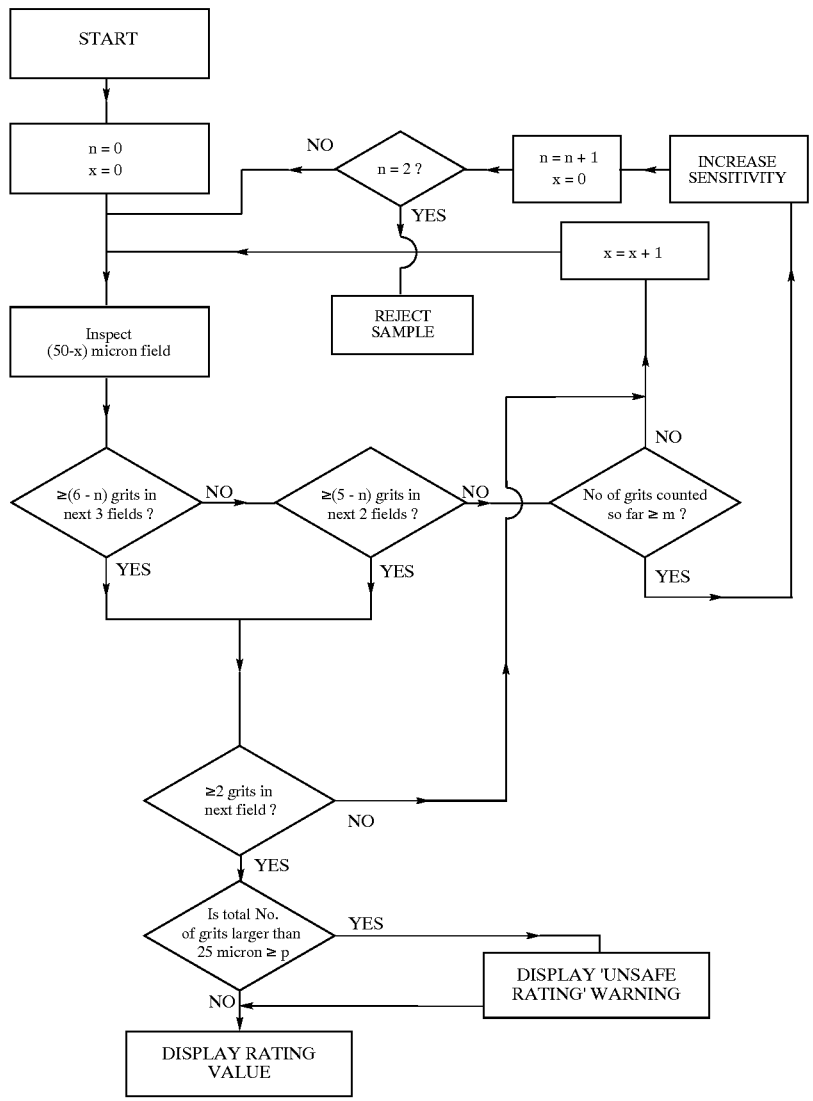

Consideration must be given to the fact that although this invention has been described and disclosed in relaton to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

What is claimed is:

1. A combination useful for assessing the fineness of dispersion of particles in a liquid vehicle, comprising:
   a) a light source;
   b) a moveable carrier having a top surface;
   c) a grindometer gauge block disposed on the top surface of said carrier, wherein said block has a longest length dimension and a flat face surface, and comprises a linear channel disposed on its face that varies in depth along said length dimension and having corresponding markings to indicate the depth of the channel, wherein said channel is adapted to receive a liquid vehicle which contains a film-forming dispersion of particles;
   d) an image-producing means, useful for producing a two-dimensional electronic image of a film disposed in said channel from a liquid vehicle placed therein;
   e) memory means for archiving said two-dimensional electronic image of said film; and
   f) means for displaying said two-dimensional image of said film, wherein said light source, said grindometer gauge block, and said image-producing means are sufficiently positioned so that the view of the image-producing means is aimed into the dark field below the light source so as to render said image-producing means disposed so that the light it receives is predominantly only that which is reflected from discontinuities in the surface of said film.

2. A combination according to claim 1 wherein said channel and said markings to indicate depth of the channel are included in said two-dimensional image.

3. A combination according to claim 1 in which the image producing means is a video camera.

4. A combination according to claim 1 wherein said image producing means is disposed so as to only receive light reflected from regions of the surface of said film which are disrupted by protruding particles.

5. A combination according to claim 1 wherein a standard achromat camera lens is disposed in the path between the light-sensing element of image-producing means and the flat surface of said grindometer block.

6. A combination according to claim 5 wherein specular reflected light derived from undisrupted regions of the surface of the film is precluded from passing, through said camera lens.

7. A combination according to claim 1 in which the image-producing means comprises a linear array of photodiodes.

8. A combination according to claim 1 in which the image-producing means is an array of charge-coupled control devices.

9. A combination according to claim 1 wherein said light source is an incandescent lamp.

10. A combination according to claim 9 wherein said light source comprises a tungsten filament.

11. A combination according to claim 9 wherein said light source emits light having wavelengths between 400 and 1100 nanometers.

12. A combination according to claim 1 wherein said light source is a biaxial compact fluorescent lamp.

13. A combination according to claim 12 wherein said light source emits light having wavelengths between 400 and 700 nanometers.

14. A combination according to claim 1 wherein the direction of view of said image producing means is aimed below the planar surface of the grindometer gauge block in any amount between 5 degrees and 20 degrees, including every degree therebetween.

15. A combination according to claim 1 wherein the view of said image producing means is aimed below the planar surface of the grindometer gauge block in an amount of 12 degrees.

16. A combination according to claim 1 wherein said means for displaying said two-dimensional image is selected from the group consisting of: cathode ray tubes and liquid crystal displays.

17. A combination according to claim 1 wherein said memory means is selected from the group consisting of: static random access memory (SRAM), dynamic random access memory (DRAM), and an array of serial/parallel access shift registers.

18. A combination useful for assessing the fineness of dispersion of particles in a liquid vehicle, comprising:
   a) a light source;
   b) a moveable carrier having a top surface;
   c) a grindometer gauge block disposed on the top surface of said carrier,
wherein said block has a longest length dimension and a flat face surface, and comprises a linear channel disposed on its face that varies in depth along said length dimension and having corresponding markings to indicate the depth of the channel, wherein said channel is adapted to receive a liquid vehicle which contains a film-forming dispersion of particles;
   d) an image-producing means, useful for producing a two-dimensional electronic image of a film disposed in said channel from a liquid vehicle placed therein;
   e) memory means for archiving said two-dimensional electronic image of said film;
   f) means for displaying said two-dimensional image of said film; and
   g) means for analyzing said two-dimensional image,
wherein said light source, said grindometer gauge block, and said image-producing means are sufficiently positioned so that the view of the image-producing means is aimed into the dark field below the light source so as to enable the image-producing means predominantly to receive light reflected from regions of the surface of said film which are disrupted by protruding particles.

19. A combination according to claim 18 wherein said channel includes a dispersion of particles in a liquid vehicle, wherein some of the particles are at least equal to the depth of said channel at some point along the channel and thus protrude above the surface of said liquid vehicle and comprise in the resulting image discrete particles, wherein said means for analyzing provides enumeration of every discrete particle.

20. A method for assessing the fineness of dispersion of particles in a liquid vehicle comprising the steps of:
   a) drawing down a sample of a dispersion of particles in a liquid vehicle to form a film of increasing thickness on a grindometer block, said grindometer block comprising a planar flat face surface;
   b) illuminating said film with a light source;
   c) generating an electronic image of said film using an image-producing means,
wherein the view of said image-producing means is aimed below the planar surface of the grindometer block in any amount between 5 degrees and 20 degrees, including every degree therebetween;
   d) storing said electronic image in computer memory selected from the group consisting of: SRAM, DRAM, or an array of shift registers so as to form a stored electronic image;
   e) viewing said stored electronic image.

21. A process according to claim 20, further comprising the step of:
   f) analyzing said stored electronic image to determine the degree of dispersion of particles in said sample of a dispersion of particles.

22. A process according to claim 20 wherein said image-producing means is disposed so that the light it receives is predominantly only that which is reflected from discontinuities in the surface of said film.

23. A process according to claim 20 wherein said image producing means is a video camera having a lens, and wherein said camera is disposed to effectively preclude specular reflected light derived from undisrupted regions of the surface of the film from entering said lens.

* * * * *